US012734134B2

(12) United States Patent
Awasthi

(10) Patent No.: US 12,734,134 B2
(45) Date of Patent: Sep. 15, 2026

(54) HERBAL BIOACTIVES BASED IMMUNOSTIMULANT FORMULATION FOR POULTRY BIRDS AND CATTLE AND PREPARATION THEREOF

(71) Applicant: Edhas Technologies Inc., Saratoga, CA (US)

(72) Inventor: Anupam Awasthi, Saratoga, CA (US)

(73) Assignee: EDHAS TECHNOLOGIES INC., Saratoga, CA (US)

( * ) Notice: Subject to any disclaimer, the term of this patent is extended or adjusted under 35 U.S.C. 154(b) by 409 days.

(21) Appl. No.: 18/358,455

(22) Filed: Jul. 25, 2023

(65) Prior Publication Data

US 2025/0032423 A1 Jan. 30, 2025

(51) Int. Cl.

| | |
|---|---|
| ***A61K 9/50*** | (2006.01) |
| ***A61K 31/05*** | (2006.01) |
| ***A61K 31/085*** | (2006.01) |
| ***A61K 31/12*** | (2006.01) |
| ***A61K 31/575*** | (2006.01) |
| ***A61P 37/04*** | (2006.01) |

(52) U.S. Cl.

CPC .......... *A61K 9/5089* (2013.01); *A61K 9/5036* (2013.01); *A61K 9/5052* (2013.01); *A61K 31/05* (2013.01); *A61K 31/085* (2013.01); *A61K 31/12* (2013.01); *A61K 31/575* (2013.01); *A61P 37/04* (2018.01)

(58) Field of Classification Search

CPC .. A61K 9/5089; A61K 9/5036; A61K 9/5052; A61K 31/05; A61K 31/085; A61K 31/12; A61K 31/575; A61P 37/04

See application file for complete search history.

(56) References Cited

U.S. PATENT DOCUMENTS

| | | | | |
|---|---|---|---|---|
| 2003/0193102 A1* | 10/2003 | Yan | A61K 9/501 | 264/4.1 |
| 2009/0117194 A1* | 5/2009 | Burja | A61P 39/06 | 424/490 |
| 2010/0113373 A1* | 5/2010 | Phillips | A61P 31/16 | 435/375 |
| 2011/0189303 A1* | 8/2011 | Yamka | A61P 29/00 | 424/639 |

(Continued)

OTHER PUBLICATIONS

Adebayo et al., "The anti-inflammatory and antioxidant activity of 25 plant species used traditionally to treat pain in southern African", BMC Complementary and Alternative Medicine (2015) 15:159—DOI 10.1186/s12906-015-0669-5.

(Continued)

*Primary Examiner* — Jianfeng Song
(74) *Attorney, Agent, or Firm* — INNOVATION CAPITAL LAW GROUP, LLP; Vic Lin

(57) ABSTRACT

A stable and highly bioavailable herbal bioactives-based immuno-stimulant formulation can boost the immune system, combat infections, and enhance growth and performance in poultry birds and cattle. A method of preparing a stable and highly bioavailable herbal bioactives-based immuno-stimulant formulation includes converting the plant bioactive molecules to multi molecular colloids using an ultra-sonication process followed by the stabilization of said colloidal particles through steric interactions.

9 Claims, 8 Drawing Sheets

(56) References Cited

U.S. PATENT DOCUMENTS

| | | | | |
|---|---|---|---|---|
| 2021/0315250 | A1* | 10/2021 | Fenzl | A61K 45/06 |
| 2023/0066836 | A1* | 3/2023 | Ben-Dor | A61K 33/30 |

OTHER PUBLICATIONS

Chang et al., "Antioxidant Activity of Extracts from Acacia confusa Bark and Heartwood", J. Agric. Food Chem. 2001, 49, 3420-3424.
Griffin, "Classification of Surface-Active Agents by HLB", Journal of Cosmetic Science, 1, 311-326 (1949).
Mosmann, "Rapid Colorimetric Assay for Cellular Growth and Survival: Application to Proliferation and Cytotoxicity Assays", Journal of Immunological Methods, 65 (1983) 55-63.
Schelz et al., "Antimicrobial and antiplasmid activities of essential oils", Fitoterapia 77 (2006) 279-285.

* cited by examiner

HERBAL BIOACTIVES BASED IMMUNOSTIMULANT FORMULATION FOR POULTRY BIRDS AND CATTLE AND PREPARATION THEREOF

BACKGROUND OF THE INVENTION

1. Field of the Invention

Embodiments of the present invention relate to a stable and highly bioavailable herbal bioactive-based immuno-stimulant formulation for boosting the immune system, enhancing growth and combating infections in poultry birds and cattle. Further embodiments of the present invention also relate to the preparation of a stable, highly bioavailable herbal bioactive-based immuno-stimulant formulation.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Poultry is one of the most widespread food industries worldwide. Chicken is the most commonly farmed species, with over 90 billion tons of chicken meat and 89 million tons of eggs produced per year. Similarly, the global demand for meat and dairy products has increased dramatically in recent decades.

Historically, antimicrobials have been used as growth promoters since 1950, when it was discovered that small, sub-therapeutic quantities of antibiotics, such as penicillin and tetracycline, delivered to animals in feed, could enhance the weight of poultry, swine, and beef cattle.

Antibiotic resistance is the ability of an organism to resist the killing effects of an antibiotic to which it was normally susceptible, and it has become an issue of global interest. Antimicrobial resistance is a global threat in animal and human medicine. Its dangers lie mainly in the failure to successfully treat patients/animals infected with antibiotic-resistant pathogens and in the high risk of transmission of such resistant pathogens.

A large diversity of antimicrobials is used to raise poultry and cattle in most countries. The indiscriminate use of such essential antimicrobials in animal production is likely to accelerate the development of antibiotic resistance in pathogens, as well as in commensal organisms. This would result in treatment failures, economic losses and could act as a source of a gene pool for transmission to humans.

Resistant bacteria can be transferred from poultry products to humans via consuming or handling meat contaminated with pathogens. Once these pathogens are in the human system, they could colonize the intestines and the resistant genes could be shared or transferred to the endogenous intestinal flora, jeopardizing future treatments of infections caused by such organisms.

The use of antibiotics in poultry and livestock production is favorable to farmers and the economy as well because it has generally improved poultry performance effectively and economically but at the same time, the likely dissemination of antibiotic resistant strains of pathogenic and non-pathogenic organisms into the environment and their further transmission to humans via the food chain could lead to serious consequences on public health.

The estimated death rate due to antibiotic resistance in humans by 2030 would be about 10 million. This figure matches the annual death toll of cancer.

Currently antibiotics like Aminoglycosides, Bambermycin, Betalactons, Quinolones, Sulfonamides, Streptogramins, and the like, are used at different growth stages to prevent and treat the bacterial diseases. The routine use of antibiotics has given rise to multiple resistant pathogens or super bugs. Due to resistance, the frequency and dose of antibiotics used in poultry birds is rising, resulting in the cost escalation in the poultry industry.

Some efforts have been made to develop alternatives to the use of antibiotics, however, to date, there is no satisfactory substitute for them.

Plants with potent antimicrobial activity can serve as a best alternate for antibiotics as they contain compounds like quinones, terpenes, tannins, terpenoids, alkaloids, and the like.

Plant bioactive molecules have numerous beneficial effects including immunomodulation, anti-inflammatory, anti-microbial, anti-depression, and the like. However, the bio-actives molecules have various disadvantages, such as poor stability to heat and light, very low bioavailability and reduction in the efficacy of the bioactive molecules while passing through the gastrointestinal tract with varying pH.

In view of the foregoing, there is a need for formulations that have immunomodulating activity besides acting as an anti-microbial in poultry birds and cattle.

SUMMARY OF THE INVENTION

Colloidal carriers have tremendous potential to overcome the above disadvantages. Goodness of plant bioactives and colloidal systems can be combined to combat infections and multi drug resistance pathogens in poultry and cattle farming. This demands the development of advanced immune modulating formulations with higher stability and bioavailability in birds and animals.

Aspects of the present invention can overcome the problems mentioned above and other problems in the art by providing a stable and highly bioavailable herbal bioactive-based immunostimulant formulation for boosting immune system, combating infections, enhancing growth, performance and quality of produce in poultry birds and cattle.

Aspects of the present invention are directed to the process of developing a multi molecular colloidal formulation that has immunomodulating activity besides acting as an anti-microbial in poultry birds and cattle.

Accordingly, in one embodiment, the present invention provides a formulation or herbal formulation comprising plant bioactive molecules and essential amino acids in a definite ratio, encapsulated in a polymer composite, wherein the plant bioactive molecules are selected from curcumin, withanolides, thymol and eugenol or curcumin, safed musli extract, thymol and oregano oil.

Accordingly in another embodiment, the invention provides a method of preparation of the stable immuno-stimulant formulation comprising steps: (a) preparing active ingredients blend encapsulated in polysorbate, wherein the active ingredients comprise curcumin, withanolides, thymol and eugenol or curcumin, safed musli extract, thymol and oregano oil (b) preparing the polymer matrix using chitosan and whey protein. (c) preparing the amino acid mixture of glycine, lysine, glutamine and tryptophan in water, (d) adding the active ingredient blend encapsulated in polysorbate obtained in step (a) to the polymer matrix obtained in step (b), (e) adding amino acid mixture obtained from step (c) to the solution of step (d) and homogenizing, (f) subjecting the solution of step (e) to sonication to ensure homogenized particle distribution and (g) optionally adding anti-microbial agents in the solution obtained in step (f) prior to bottling.

In still another embodiment, the present invention provides a stable and bioavailable herbal formulation with a particle size in the range of 10-100 nm.

In yet another embodiment, the present invention provides administration of the formulation for providing at least one benefit of increasing the innate immunity in poultry birds and cattle and inhibiting the disease-causing pathogens.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

FIG. 5A is control, FIG. 5B is at 12.5 μg/ml, FIG. 5C is at 25 μg/ml, FIG. 5D is at 50 μg/ml, FIG. 5E is at 100 μg/ml and FIG. 5F is at 200 μg/ml;

Figure 1:
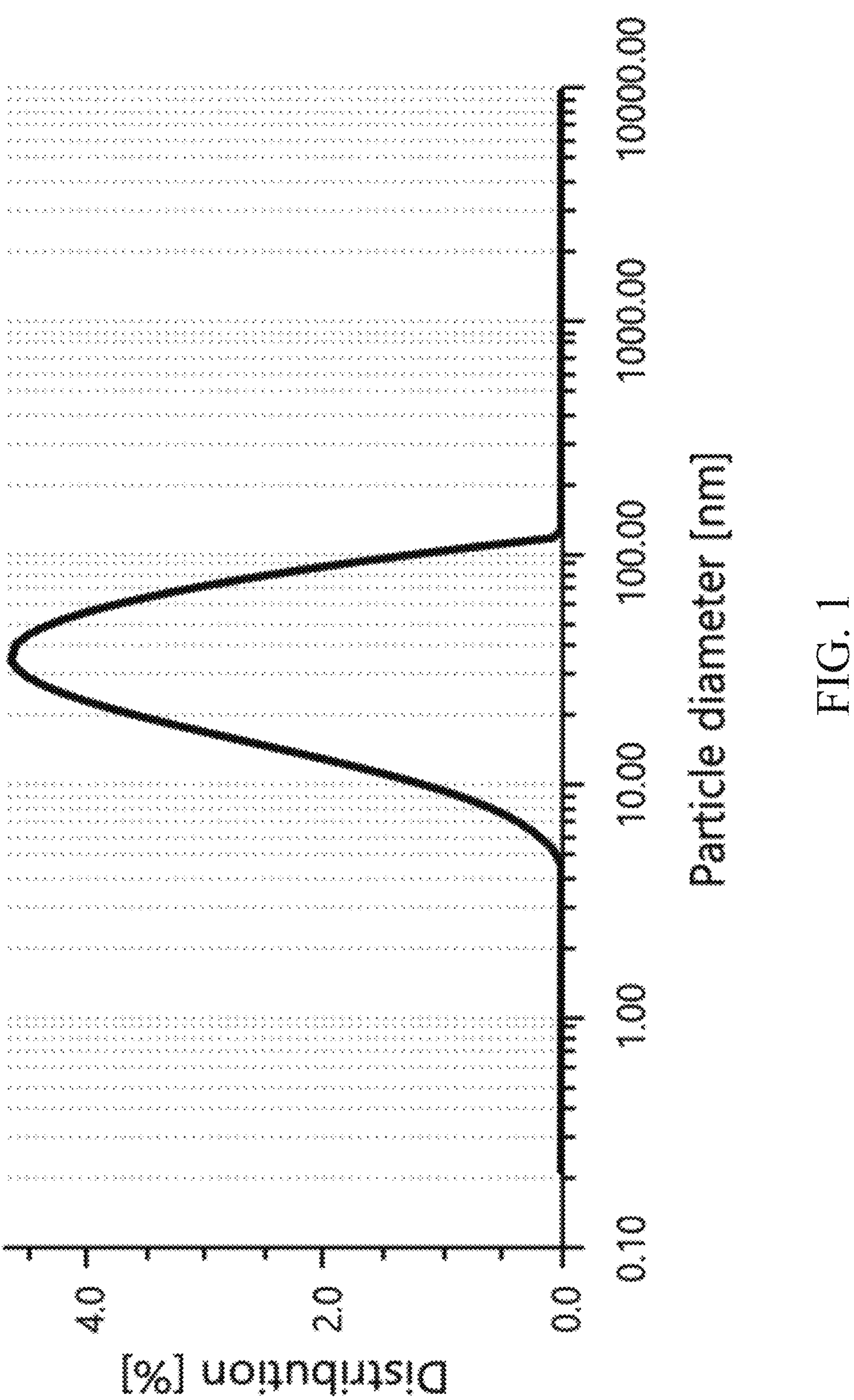
FIG. 1 shows the particle size distribution of an immunostimulant formulation according to an embodiment of the present invention.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising." when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

As is well known to those skilled in the art, many careful considerations and compromises typically must be made when designing for the optimal configuration of a commercial implementation of any process or formulation, and in particular, the embodiments of the present invention. A commercial implementation in accordance with the spirit and teachings of the present invention may be configured according to the needs of the particular application, whereby any aspect(s), feature(s), function(s), result(s), component (s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide a stable and highly bioavailable herbal bioactives-based immuno-stimulant formulation that can boost the immune system, combat infections, and enhance growth and performance in poultry birds and cattle. A method of preparing a stable and highly bioavailable herbal bioactives-based immuno-stimulant formulation includes converting the plant bioactive molecules to multi molecular colloids using an ultra-sonication process followed by the stabilization of said colloidal particles through steric interactions.

Plants with potent antimicrobial activity can serve as a best alternative for antibiotics as they contain compounds like quinones, terpenes, tannins, terpenoids, alkaloids and the like. Goodness of plant bioactives and colloidal systems can be combined to combat infections and multi drug resistance pathogens in poultry and cattle farming.

Aspects of the present invention, as discussed in greater detail below, adopt a strategy of creating a unique formulation by incorporating multiple anti-microbial and immune-stimulant molecules in a polymer matrix.

The present formulation can prevent poultry infections via immune-stimulating effect.

The process of developing the formulation is unique, ensuring high efficacy against antibiotic resistance pathogenic bacteria, even at lower concentration, and can assist in maintaining the balance of Th1/Th2. The Th1 and Th2 cells play an important role in immunity. Th1 cells stimulate cellular immune response, participate in the inhibition of macrophage activation and stimulate B cells to produce IgM, IgG1. Th2 stimulates humoral immune response, promotes B cell proliferation and induces antibody production (IL-4).

Aspects of the present invention relate to a plant bioactive-based immunostimulant herbal formulation for enhancing the immunity in poultry birds and cattle, as well as the preparation of such formulations.

In an embodiment, the present invention provides a formulation or herbal formulation comprising plant bioactive molecules and essential amino acids in a definite ratio encapsulated in a polymer composite.

In a non-limiting embodiment, the bioactive or active molecules comprises curcumin, withanolides, thymol and eugenol.

In an alternative non-limiting embodiment, the bioactive or active molecules comprises curcumin, safed musli extract, thymol and oregano oil.

In a non-limiting embodiment, the amino acids includes glycine, lysine, tryptophan, glutamine among others or mixture thereof.

In a non-limiting embodiment, the polymer composite of chitosan and whey protein of varying ratios is used for encapsulation.

The stable formulation can be produced by judiciously converting the plant bioactive molecules to colloids of a size less than 100 nm using an ultra-sonication process, followed by stabilization of said colloidal particles through steric interactions. The resulting stabilized colloidal particles can then be surface modified using proteins, polysorbates and/or biopolymers.

The formulation has functional molecules like curcumin, withanolides, thymol and eugenol or curcumin, safed musli extract, thymol and oregano oil that are stabilized within a peptide-polymer composite using whey protein and chitosan.

Without limiting or bounding to any theory, chitosan aids in the smart delivery of the active molecules and chitosan itself has anti-fungal properties that adds value to the formulation. The formulation has been designed to prevent any infection via innate immunity besides promoting growth.

In a non-limiting embodiment, the concentration of the major functional molecules such as curcumin is in the range of 2000 to 5000 ppm, withanolides is in the range of 2000 to 3000 ppm, thymol is in the range of 3000 to 5000 ppm and eugenol is in the range of 2000 to 3000 ppm.

In a non-limiting embodiment, the amino acids can be added in the range of 1000 to 5000 ppm, either alone or in combination.

In a non-limiting embodiment, glycine, lysine, glutamine and tryptophan are added in the ratio of 5:4:2:1.

Another aspect of the invention provides a method of the preparation of the stable immuno-stimulant formulation, comprising the steps:

(a) preparing an active ingredients blend encapsulated in polysorbate, wherein the active ingredients comprise curcumin, withanolides, eugenol and thymol, the preparation comprises the steps of:
  i. dissolving curcumin in polysorbates with sonication;
  ii. dissolving withanolides in water;
  iii. dissolving thymol and eugenol in a suitable solvent; and
  iv. adding solution (ii) to (i) followed by solution (iii) and thoroughly homogenizing using high sheer homogenizer;
(b) preparing the polymer matrix using chitosan and whey protein;
(c) preparing the amino acid mixture of glycine, lysine, glutamine and tryptophan in water;
(d) adding the active ingredients blend encapsulated in polysorbate obtained in step (a) to the polymer matrix obtained in step (b);
(e) adding amino acid mixture obtained from step (c) to the solution of step (d) and homogenizing;
(f) subjecting the solution of step (e) to sonication to ensure homogenized particle distribution; and
(g) optionally adding anti-microbial agents in the solution obtained in step (f) prior to bottling.

In an alternative non-limiting embodiment, the method of preparation of the stable immuno-stimulant formulation of the present invention comprises using the active ingredients curcumin, safed musli extract, thymol and oregano oil in step (a) and making necessary changes in the process parameters.

In a non-limiting embodiment, the step (a) (i) comprises dissolving curcumin in the weight percentage range of 0.2 to 0.5% in polysorbates.

In a non-limiting embodiment, the step (a) (ii) comprises dissolving withanolides in the weight percentage range of 0.2 to 0.3% in water.

In a non-limiting embodiment, in the step (a) (iii), the suitable solvent is selected from alcohols, such as methanol, ethanol, isopropanol, aryl alcohols or mixture thereof, and other such suitable solvent systems known in the art.

In a non-limiting embodiment, in the step (a) (iii), the weight percentage of thymol and eugenol is in range of 0.3 to 0.5% and 0.2 to 0.3%, respectively, and the suitable solvent is ethanol.

In a non-limiting embodiment, the step (b) comprises using 0.1% (w/v) chitosan and 0.05% (w/v) whey protein in the ratio of 2:1.

In a non-limiting embodiment, the step (c) comprises using an amino acid mixture of glycine, lysine, glutamine and tryptophan in the ratio of 5:4:2:1.

In a non-limiting embodiment, in the step (c), i.e., the preparation of the amino acid mixture, can be done separately or in another preparation container/vessel or prepared in situ before use.

In a non-limiting embodiment, in the step (e) the homogenizing is performed at 600-800 rpm.

In a non-limiting embodiment, in the steps (a) and (f), the sonication is performed for 5-30 minutes, preferably 10-20 minutes.

As the particle size of the formulation is in the desirable range, the bioavailability and efficiency are high.

The HLB (hydrophilic-lipophilic balance) of the formulation can be maintained between 11 and 13, providing greater stability to the formulation and, in turn, improved efficiency. The HLB is calculated using the molecular weight of hydrophilic molecules in the formulation divided by total mass and multiplied by 20 (Griffin's method).

Embodiments of the present invention relate to an herbal formulation with a particle size in the sub-micron range.

The particle size of the immunostimulant formulation can be measured based on the principle of dynamic light scattering in a particle size analyzer.

In a non-limiting embodiment, the mean hydrodynamic diameter or particle size of the immuno-stimulant formulation is in the range of 10-100 nm. (see FIG. 1)

In a non-limiting embodiment, the particle size of the active/functional molecule alone i.e., for instance, curcumin, withanolides, thymol and eugenol is measured between 10-50 nm.

The poly dispersion index is determined using the method known to the person skilled in the art. This index is used to determine the dispersion uniformity of the active molecules.

In a non-limiting embodiment, the poly-dispersion index (PI) of the herbal formulation is 0.1 to 0.5, indicating the uniform dispersion of the active molecules in the formulation.

The formulation stability can be confirmed by analyzing the zeta potential. The positive and negative charge of the zeta potential is directly proportional to the surface charge of the sample.

Figure 2:
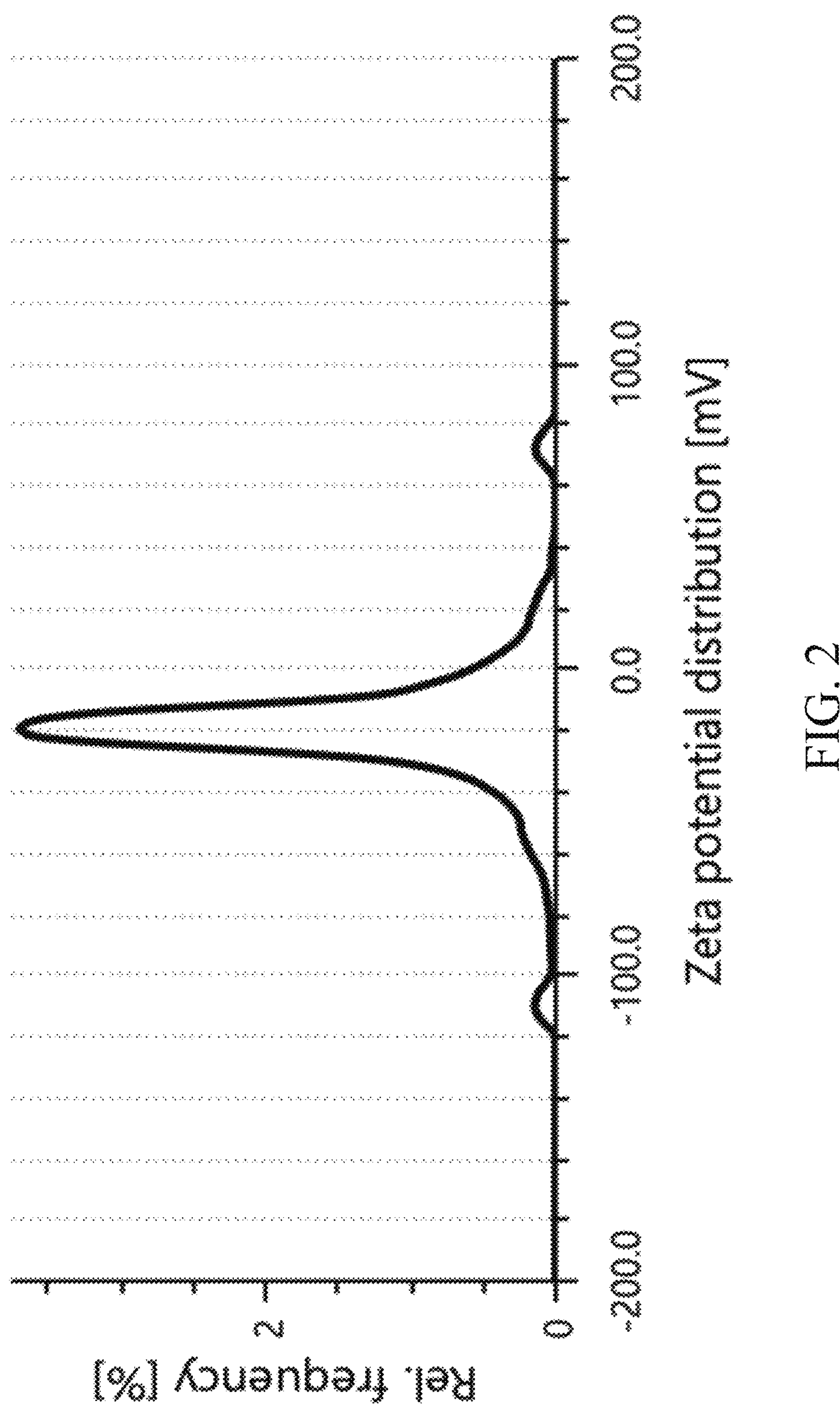
FIG. 2 shows the zeta potential of active ingredients encapsulated within a micelle.
Figure 3:
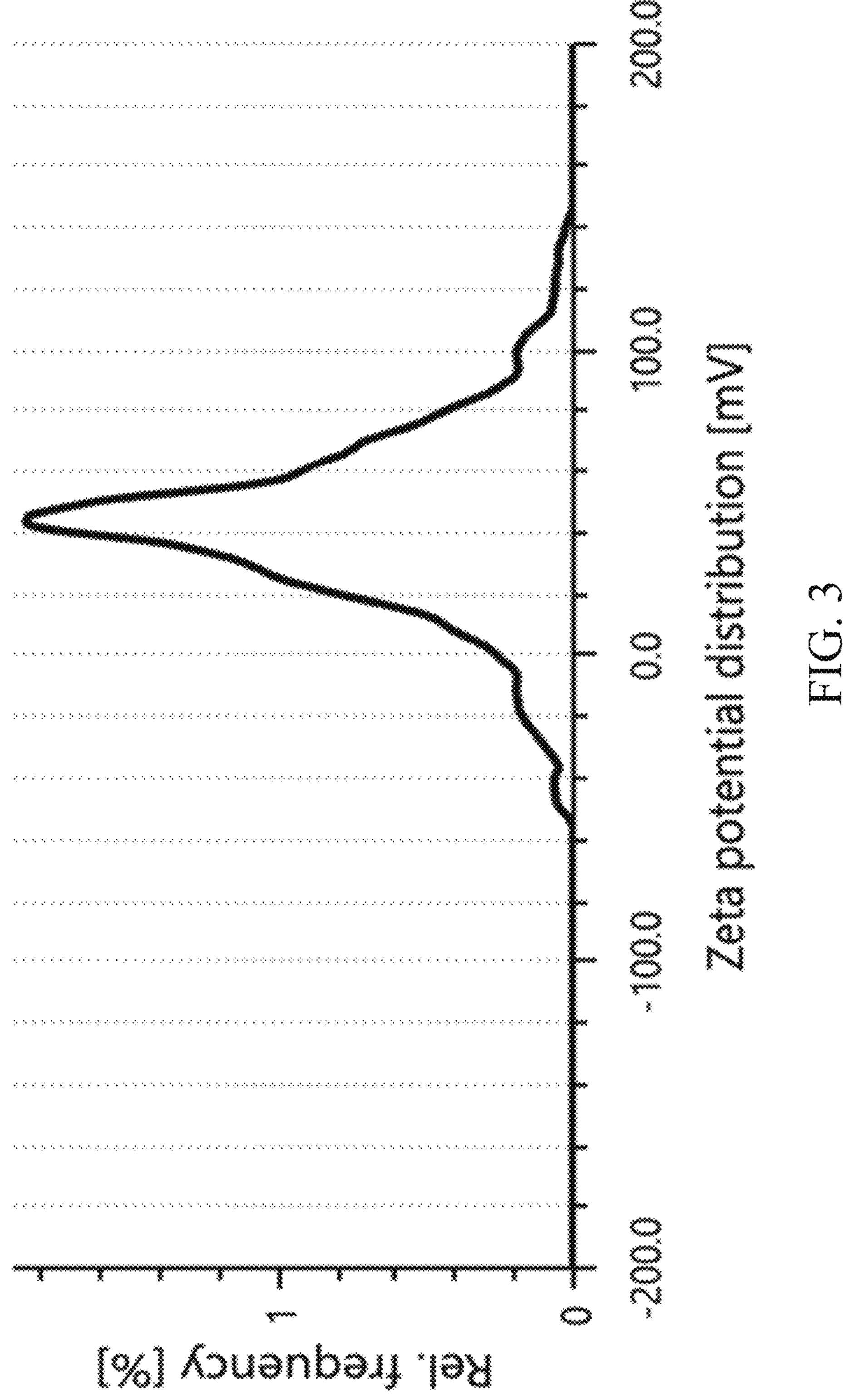
FIG. 3 shows the zeta potential of a final immunostimulant formulation, according to an embodiment of the present invention.

In a non-limiting embodiment, illustrative FIG. 2 shows that the zeta potential of the active ingredients (−21 mV) is negative. The formulation is further stabilized using the positively charged polymer composite and hence, the zeta potential of final formulation is above +30 mV to +40 mV (FIG. 3).

The chitosan and whey protein composite, used to stabilize the active ingredients, can be positively charged and thus, the positive charge of the final formulation indicates that the active ingredients are stabilized by the polymer matrix.

In an embodiment, the immunostimulant formulation of the present invention has anti-inflammatory and anti-oxidant activities with less cyto-toxicity.

Another aspect of the invention provides a method of treating poultry birds and cattle to enhance the immunity comprising administering an effective amount of the immunostimulant herbal formulation to one or more poultry birds and cattle.

In a non-limiting embodiment, the poultry bird is selected from chicken, turkey, duck, goose, guinea fowl, quail and pigeon.

In a non-limiting embodiment, the cattle is selected from cow, ox, bull, calf, sheep and goat.

In a non-limiting embodiment, the administration of the formulation provides at least one benefit of increasing the innate immunity in poultry birds and inhibiting the disease-causing pathogens.

In an embodiment, the administration of the formulation increases the innate immunity by maintaining the balance of Th1/Th2.

In an embodiment, the administration of the formulation prevents and/or treats diseases such as Newcastle disease, avian influenza (bird flu), salmonella disease, and Marek's disease, among others.

In an embodiment, the formulation can be administered orally or through any other suitable route of administration.

In a non-limiting embodiment, the dosage of the formulation is from about 300 to 500 μl per kg of the body weight of the poultry bird.

In a non-limiting embodiment, the dosage is applied as two doses during the starter phase and two doses during the grower phase, at a 5 days interval.

The quantification of curcumin in the formulation can be performed using UV-Vis spectroscopy, where the quantity of the curcuminoids is estimated using UV-Vis spectroscopy and the percentage is calculated using the formula: Concentration (x)=((Absorbance (y)−Intercept)/Slope)*dilution factor.

In a non-limiting embodiment, the concentration of curcumin in the formulation is 3157 ppm.

The synergy effect of compositions in the formulation can be determined, where the fractional inhibitory concentration index (FICI) was used to determine the interaction of the two drugs in combination, and the results were interpreted according to the conventional methods. The following formula was used for the calculation:

$$FICI = (MICA \text{ in combination}/MICA \text{ alone}) + (MICB \text{ in combination}/MICB \text{ alone}).$$

Where, *MIC* is minimum inhibitory concentration.

The effects of the antimicrobial drug combinations were classified according to the following criteria:

(1) FICI≤0.5, synergistic effects;

(2) 0.5<FICI≤1, additive effects;

(3) 1<FICI<4, no interactions; and (4) FICI≥4.0, antagonistic effects.

The formulations with and without some active ingredients are tested for FICI against *Pseudomonas aeruginosa*, and the results are as follows.

Table 1, below, shows the FICI of bioactives in an immuno-stimulant formulation with and without Eugenol against *Pseudomonas aeruginosa*.

TABLE 1

| Sample | MIC | FICI |
|---|---|---|
| Eugenol Alone (A) | 10.09 mg/ml | 0.38 |
| Curcumin Alone (B) | 8.1 mg/ml | |
| Formulation with all active ingredients | 1.3 mg/ml | |
| Formulation without Eugenol | 2.1 mg/ml | |

*All values are mean of three replications

Table 2, below, shows the FICI of bioactives in an immuno-stimulant formulation with and without Thymol against *Pseudomonas aeruginosa*.

TABLE 2

| Sample | MIC | FICI |
|---|---|---|
| Thymol Alone (A) | 9.2 mg/ml | 0.3 |
| Curcumin Alone (B) | 8.1 mg/ml | |
| Formulation with all active ingredients | 1.37 mg/ml | |
| Formulation without Thymol | 1.97 mg/ml | |

*All values are mean of three replications

Table 3, below, shows the FICI of bioactives in an immuno-stimulant formulation with and without Withanolides against *Pseudomonas aeruginosa*.

TABLE 3

| Sample | MIC | FICI |
|---|---|---|
| Withanolides Alone (A) | 30 mg/ml | 0.3 |
| Curcumin Alone (B) | 8.1 mg/ml | |
| Formulation with Withanolides (Final formulation with all a.i) | 1.37 mg/ml | |
| Formulation without Withanolides | 1.35 mg/ml | |

*All values are mean of three replications

*Pseudomonas aeruginosa* displays resistance to a variety of antibiotics, including aminoglycosides, quinolones and β-lactams and it causes necropsy in chickens.

The above results indicate that the FICI in all the three cases was less than 0.5, proving the synergy between active molecules.

Raw 246.7 macrophage cell line studies were carried out to analyse the impact of the immuno-stimulant formulation, according to embodiments of the present invention, for anti-inflammation activity and cell-viability.

Preparation of Raw 246.7 macrophages cell suspension: A subculture of raw 246.7 macrophages in Dulbecco's modified eagle's medium (DMEM) was trypsinized separately, after discarding the culture medium. To the disaggregated cells in the flask, 25 mL of DMEM with 10% fetal calf serum (FCS) was added. The cells were suspended in the medium by gentle passage with the pipette followed by homogenization.

Seeding of cells: One mL of the homogenized cell suspension was added to each well of a 24-well culture plate along with different concentrations of sample (0 to 200 μg/mL) and incubated at 37° C. in a humidified $CO_2$ incubator with 5% $CO_2$. After 48 hrs of incubation, the cells were observed under an inverted tissue culture microscope. Cytotoxic assay was carried out with 80% confluence of cells.

Cytotoxicity assay: The assay was carried out using (3-(4, 5-dimethyl thiazol-2yl)-2, 5-diphenyl tetrazolium bromide (MTT). MTT was cleaved by mitochondrial succinate dehydrogenase and reductase of viable cells, yielding a measurable purple product formazan. This formazan production was directly proportional to the viable cell number and inversely proportional to the degree of cytotoxicity. After 48 h incubation, the wells were added with MTT and left for 3 h at room temperature. All the contents in the wells were removed using pipette and 100 μl sodium dodecyl sulphate (SDS) diluted in dimethyl sulfoxide (DMSO) were added to dissolve the formazan crystals, absorbance was read in Lark LIPR-9608 microplate reader at 540 nm.

Anti-inflammation assay-inhibition of nitric oxide (NO) production cell culture: The RAW 264.7 macrophage cell lines were cultured in plastic culture flasks in Dulbecco's modified eagle's medium (DMEM) containing l-glutamine supplemented with 10% fetal calf serum (FCS) and 1% antibiotic solution (Gibco, USA) under 5% $CO_2$ at 37° C. Cells were seeded in 96 well-microtitre plates and were activated via incubation in a medium containing lipopolysaccharide (LPS) (5 μg/mL) and various concentrations of the present formulation dissolved in sterile DMEM medium.

Measurement of nitrite: Nitric oxide (NO) released from macrophages was assessed by determination of nitrite concentration in the culture supernatant using Griess reagent. After 24 h incubation, 100 μL of supernatant from each well of cell culture plates was transferred into 96-well microtitre plates, and an equal volume of Griess reagent was added. The absorbance of the resultant solutions in the wells of the microtitre plate was determined with a microtitre plate reader after 10 min at 550 nm. The concentrations of nitrite were calculated from regression analysis using serial dilutions of sodium nitrite as a standard. Percentage inhibition was calculated based on the ability of extracts to inhibit nitric oxide formation by cells compared with the control (cells in media without extracts containing triggering agents), which was considered as 0% inhibition.

The in-vitro cytotoxicity activity results of the immuno-stimulant formulation of the present invention against Raw 246.7 macrophage cells, triggered the cytotoxicity with increasing sample concentration is presented below in Table 4.

TABLE 4

| Concentration (μg/ml) | R1 | R2 | R3 | Avg | Control | Cell viability (%) |
|---|---|---|---|---|---|---|
| 0.0 | 1.366 | 1.354 | 1.327 | 1.349 | 1.349 | 100.00 |
| 12.5 | 1.364 | 1.325 | 1.301 | 1.330 | 1.349 | 98.59 |
| 25.0 | 1.223 | 1.271 | 1.197 | 1.230 | 1.349 | 91.20 |
| 50.0 | 1.087 | 1.116 | 1.022 | 1.075 | 1.349 | 79.69 |
| 100.0 | 0.987 | 0.957 | 0.846 | 0.930 | 1.349 | 68.94 |
| 200.0 | 0.687 | 0.537 | 0.571 | 0.598 | 1.349 | 44.35 |

*R1, R2 and R3 are three replications for each concentration

Figure 4:
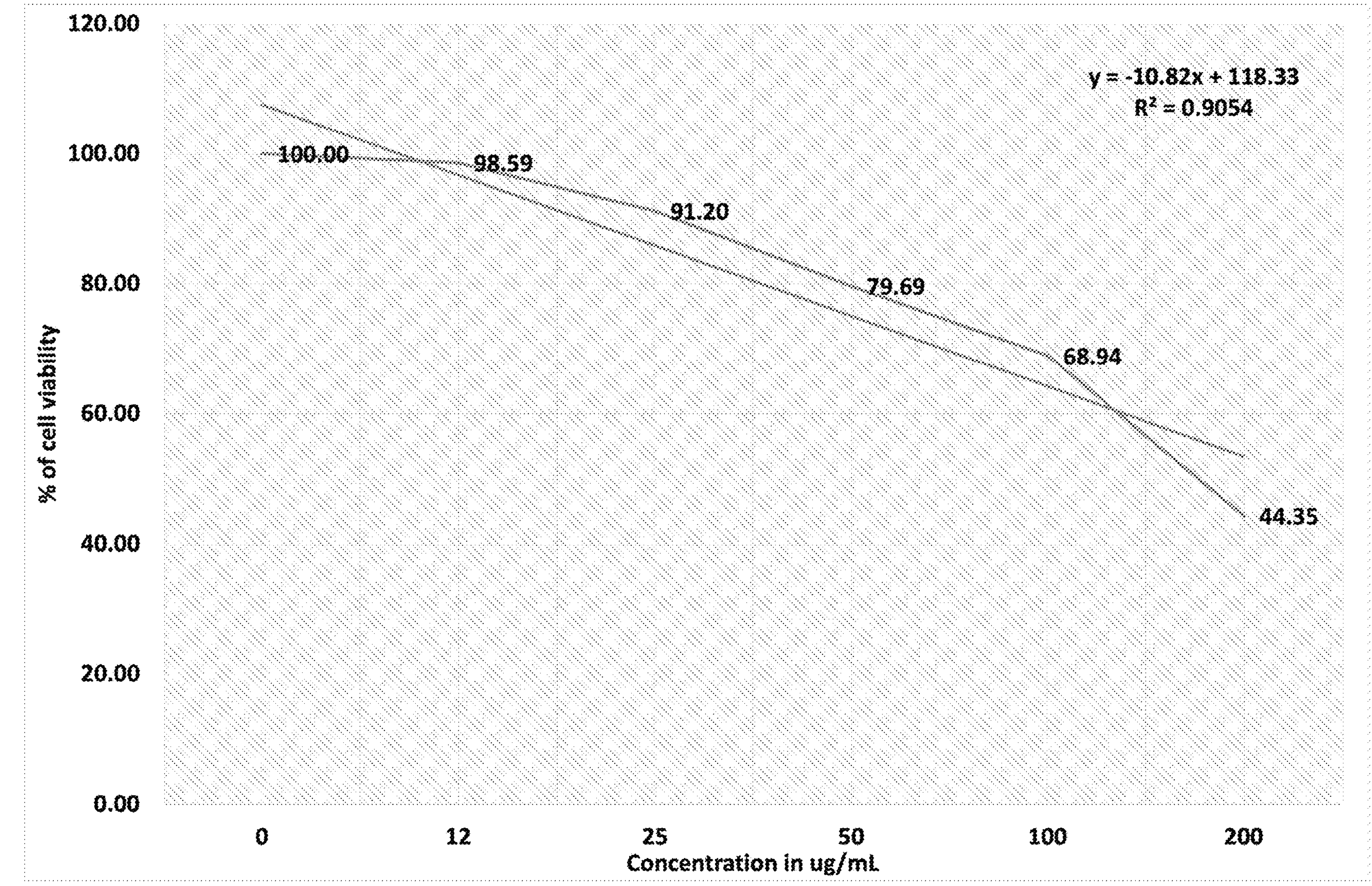
FIG. 4 illustrates the in vitro cytotoxicity effect of the immunostimulant formulation, according to embodiments of the present invention, against Raw 246.7 macrophages cell lines.
Figures 5A, 5B, 5C, 5D, 5E, 5F:
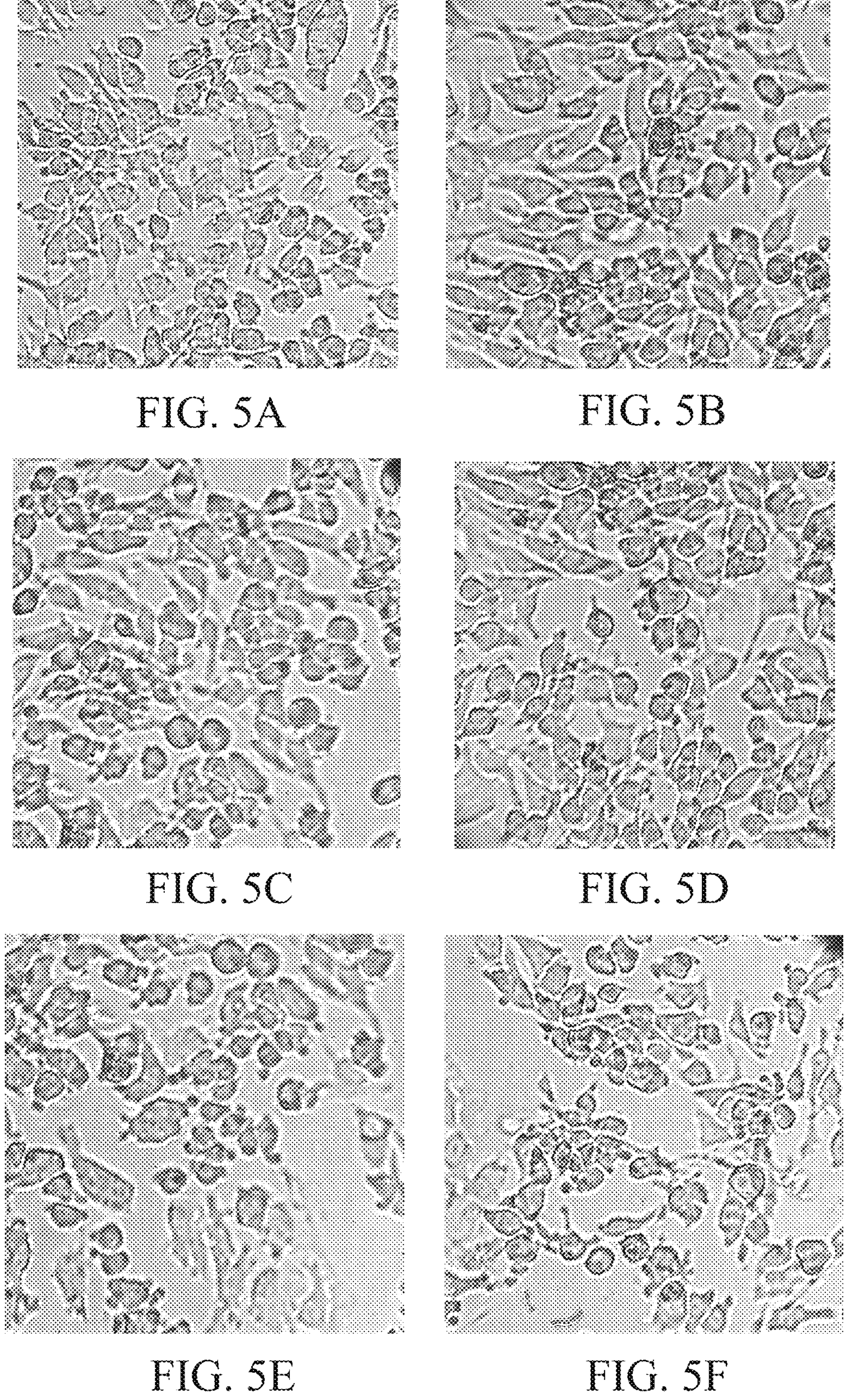
FIGS. 5A through 5F illustrates the cytotoxicity effect of the immunostimulant formulation, according to embodiments of the present invention, against Raw 246.7 macrophages cell lines, where

In the RAW 264.7 macrophage cell lines, a cytotoxicity effect was observed in present immunostimulant formulation concentrations within 48 hours of treatment (FIG. 4). It is evident that the less cytotoxicity of the present formulation showed no cell disintegration and migration after 48 h of treatment against the selected tested cell lines (FIGS. 5A through 5F). It was calculated that the $IC_{50}$ of the present immunostimulant formulation against Raw 246.7 macrophages cells is 173.29 μg/ml.

The anti-inflammatory activity of the immuno-stimulant formulation on NO inhibition by induced RAW 264.7 macrophage cell lines is presented in Table 5.

TABLE 5

| Concentration | OD | Control OD | % Inhibition |
|---|---|---|---|
| 0.0 | 0.544 | 0.544 | 0.00 |
| 12.5 | 0.494 | 0.544 | 9.19 |
| 25.0 | 0.456 | 0.544 | 16.18 |
| 50.0 | 0.421 | 0.544 | 22.61 |
| 100.0 | 0.357 | 0.544 | 34.38 |
| 200.0 | 0.298 | 0.544 | 45.22 |

Figure 6:
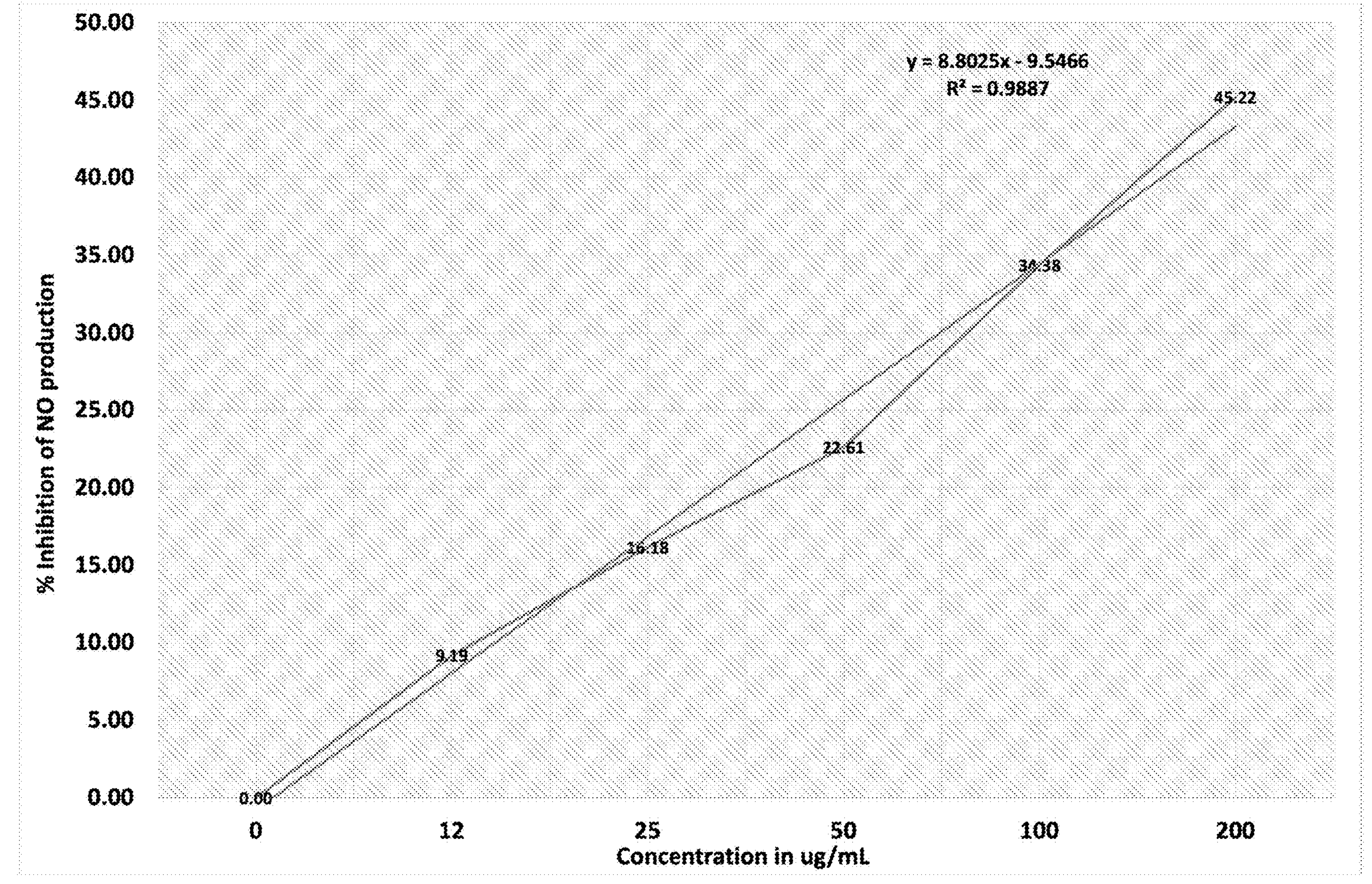
FIG. 6 illustrates the in vitro anti-inflammation effect of the immunostimulant formulation, according to embodiments of the present invention, against Raw 246.7 macrophages cell lines.

The immunostimulant formulation of the present invention has the remarkable inhibitory activity on NO production (45.22% inhibition) at 200 μg/mL (FIG. 6). The release of NO promotes inflammation, therefore the samples that could act as scavengers of NO, or inhibitors of its production, especially with corresponding low cytotoxicity could be used to mitigate the propagation of inflammation by NO.

DPPH (2, 2-diphenyl-1-picrylhydrazyl) assay was carried out to analyse the impact of immuno-stimulant formulation of the present invention for anti-oxidant activity.

The radical scavenging activity of the immune-stimulant formulation was determined by using a DPPH assay. DPPH is a dark-colored crystalline powder composed of stable free radical molecules. The decrease in the absorption of the DPPH solution after the addition of an antioxidant was measured at 517 nm. Ascorbic acid (10 mg/ml DMSO) was used as reference.

DPPH solution (100 ppm) was prepared by dissolving 0.01 g of DPPH in 100 ml of ethanol. In the test tubes, 0.5 ml of different concentrations (10, 25, 50, 100, 250 and 500 ppm) of immunostimulant formulation were taken with 4.5 ml of DPPH solution. The reaction mixture was incubated in a dark condition at room temperature for 20 min. After 20 min, the absorbance of the mixture was read at 517 nm. Three ml of DPPH solution was taken as control. The % radical scavenging activity of the plant extracts was calculated using the following formula, $$\text{DPPH scavenging effect (\%) Inhibition}=A0_{517}-A1_{517}/A0_{517}\times 100,$$

where % inhibition is the radical scavenging activity,

A0=the absorbance of control at 517 nm, and

A1=the absorbance of sample at 517 nm.

The anti-oxidant effect of the immunostimulant formulation of the present invention on DPPH (free radicle) is presented in Table 6.

TABLE 6

| S. No | Sample Concentration (ppm) | OD@517 Sample | OD@517 Control | % Inhibition by test sample | Ascorbic acid (Positive control) | % Inhibition by Ascorbic acid |
|---|---|---|---|---|---|---|
| 1 | 500 | 0.2492 | 1.731 | 85.60% | 0.1565 | 90.65% |
| 2 | 250 | 0.4321 | 1.731 | 75.00% | 0.2138 | 87.60% |
| 3 | 100 | 0.5211 | 1.731 | 69.90% | 0.4988 | 71.18% |
| 4 | 50 | 0.6798 | 1.731 | 60.72% | 0.5812 | 66.42% |
| 5 | 25 | 0.7129 | 1.731 | 58.81% | 0.6119 | 64.65% |
| 6 | 10 | 0.7931 | 1.731 | 54.18% | 0.7131 | 58.80% |

*All values are replication of three numbers

Figure 7:
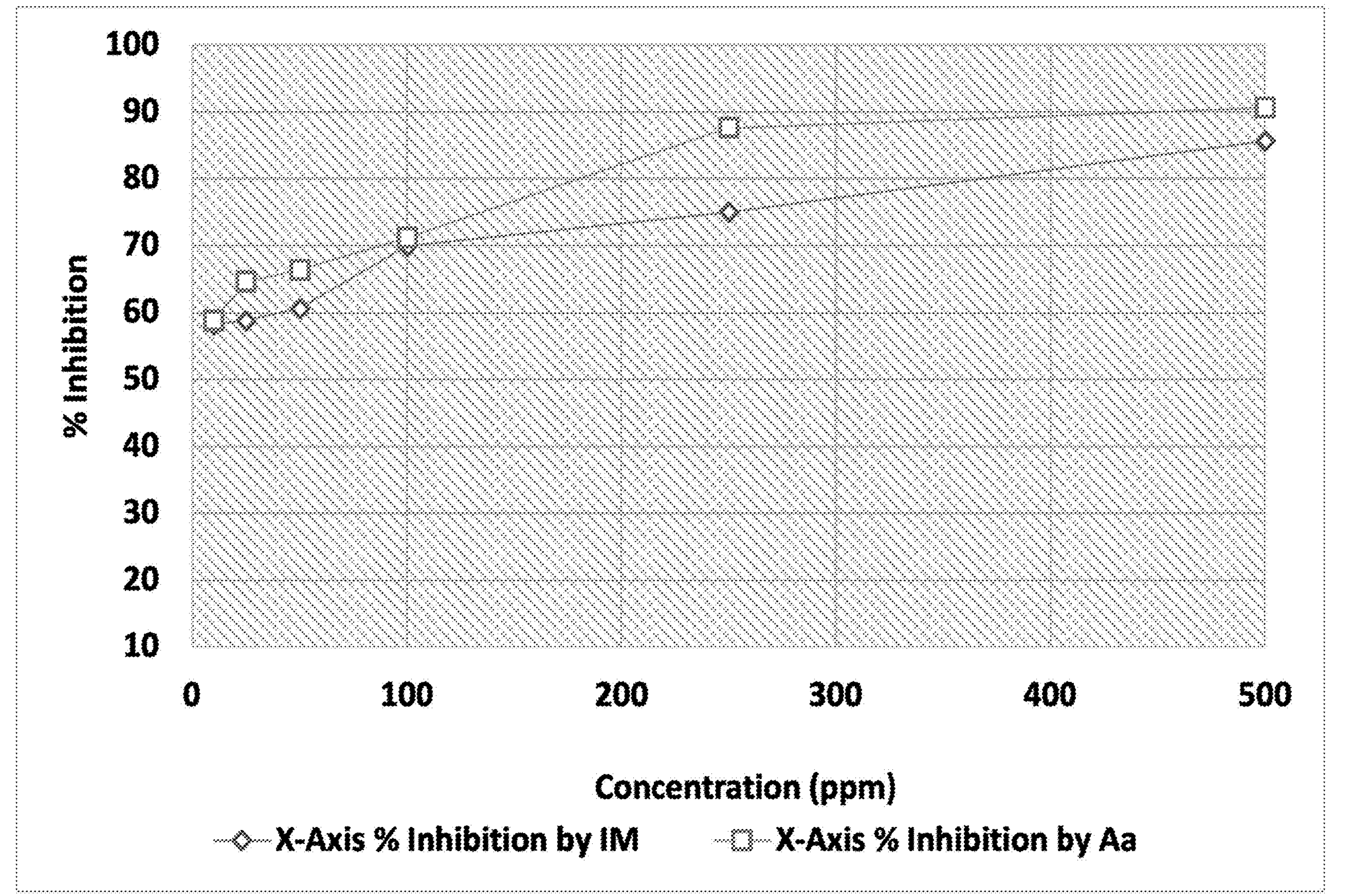
FIG. 7 illustrates the anti-oxidant effect of the immunostimulant formulation, according to embodiments of the present invention, on DPPH (free radicle)

The results clearly indicate that the test sample expresses higher anti-oxidant percentage compared with ascorbic acid (FIG. 7). $IC_{50}$ was found to be 10 ppm in case of both sample and the positive control.

ABTS [2,2-azinobis-(3-ethylbenzothiazoline-6-sulfonate)] assay was carried out to analyse the impact of immuno-stimulant formulation of the present invention for anti-oxidant activity. The results were in-line with the percent inhibition obtained from DPPH assay.

In a test tube, equal volumes of 7 mM aqueous ABTS and 2.45 mM of potassium permanganate solution was taken. The mixture was maintained in the dark at room temperature for 12-16 h until a dark blue colour was developed. The absorbance of the ABTS solution was measured to be 0.9114 at 734 nm with ethanol.

Preparation of the reaction mixture: 0.5 ml of different concentrations of the present formulation was added to 4.5 ml of the ABTS radicle solution. The reaction mixture was incubated for 30 min and absorbance was measured at 734 nm. Ethanol was taken as blank. Percent Inhibition of test sample was measured using the formula:

$$\text{ABTS+Scavenging effect (\%)}=(AB-AA)/AB)\times 100,$$

where AB=absorbance of the ABTS radicle+solvent, and

AA=absorbance of the ABTS radicle+sample.

The anti-oxidant effect of the immunostimulant formulation of the present invention on ABTS+ (stable free radicle) is presented in Table 7.

TABLE 7

| S. No | Sample Concentration (ppm) | OD@734 Sample | OD@734 Control | % Inhibition by IM | Trolox (Positive control) | % Inhibition by Trolox |
|---|---|---|---|---|---|---|
| 1 | 1000 | 0.0844 | 0.9114 | 90.73 | 0.0069 | 99.24 |
| 2 | 500 | 1.713 | 0.9114 | 81.21 | 0.0539 | 94.08 |
| 3 | 250 | 0.2439 | 0.9114 | 73.22 | 0.0991 | 89.12 |
| 4 | 100 | 0.3966 | 0.9114 | 56.48 | 0.1211 | 86.71 |
| 5 | 50 | 0.4209 | 0.9114 | 53.81 | 0.2452 | 73.1 |
| 6 | 25 | 0.5337 | 0.9114 | 41.44 | 0.3371 | 63.01 |
| 7 | 10 | 0.6142 | 0.9114 | 32.59 | 0.4148 | 54.48 |

* All values are replication of three numbers

Figure 8:
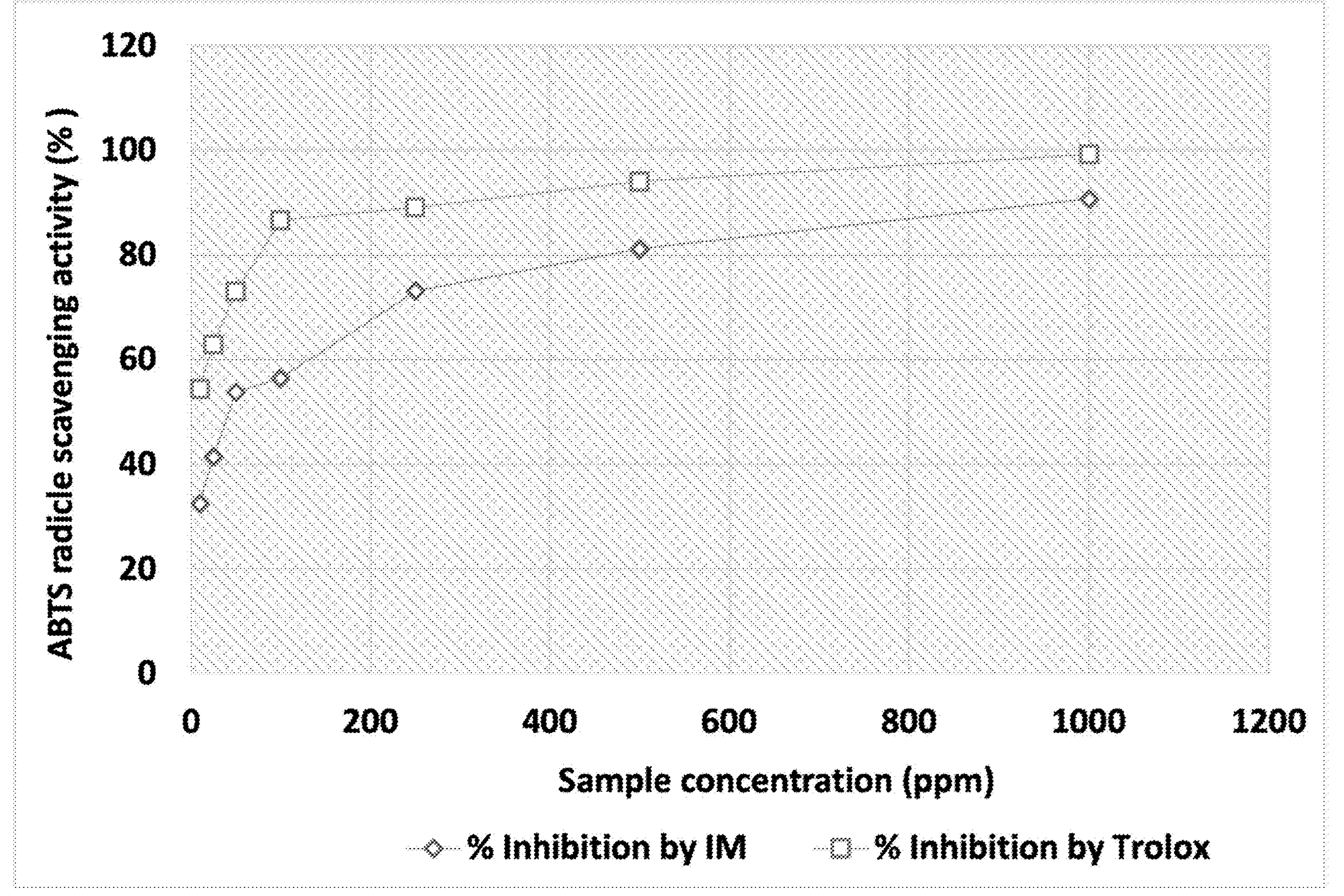
FIG. 8 illustrates the antioxidant effect of the immunostimulant formulation, according to embodiments of the present invention, on ABTS.+stable free radicle.

The results clearly indicates that the immunostimulant formulation of the present invention expresses higher anti-oxidant percentage compared with Trolox (FIG. 8), a powerful antioxidant agent was used as a reference. $IC_{50}$ was found to be 50 ppm in the case of sample and 10 ppm in the case of positive control (Trolox).

Two assays commonly used for serological testing of antibodies are hemagglutination-Inhibition (HI) and enzyme linked immune-sorbent assay (ELISA). The present formulation was tested according to these two assays to confirm the immunostimulant activity.

Hemagglutination-inhibition (HI) assay was performed in a batch of 1000 broiler birds to quantify the serum antibody titre against Newcastle disease.

The HI test was performed before feeding the broilers with immunostimulant formulation, out of which, more than 50% of the infected broilers were recorded with the antigen titre of 16 and more than 20% recorded antigen titre less than 16. Then, the infected broilers were fed with immunostimulant formulation at 300 μl/bird, 400 μl/bird and 500 μl/bird dilutions. The whole blood samples were collected on $21^{st}$ and $42^{nd}$ day from which serum were separated for the HI assay.

The study revealed that the antibody titre in both pre-starters and starters are showing protective titre of ≥24, which indicates that the immunostimulant formulation has significance potency against Newcastle disease of broilers.

Enzyme linked immune-sorbent assay (ELISA) kit was used to measure the amount of antibody to Newcastle disease virus (NDV) in the serum collected from broilers on $21^{st}$ and $42^{nd}$ day. It works on the principle where any anti-NDV antibodies present in the chicken serum will bind and form an antigen-antibody complex. A yellow color is developed if anti-NDV antibody is present and the intensity is related to the amount of anti-NDV antibody present in the sample. The results of antibody levels in the serum of broilers obtained in ELISA are presented below.

Table 8, below, shows the antibody levels in the serum of broilers obtained in ELISA.

TABLE 8

| Treatment | 21st day (Starters) | 42nd day (Pre starters) |
|---|---|---|
| Control | 617 | 1107 |
| T1 (300 μl) | 992 | 4987 |
| T2 (400 μl) | 1013 | 5534 |
| T3 (500 μl) | 1137 | 5529 |

*All values are mean of three replications and the dose administered are for per kg of body weight of the bird
T1- 300 μl of immunostimulant formulation/bird
T2- 400 μl of immunostimulant formulation/bird
T3- 500 μl of immunostimulant formulation/bird The increase in mean antibody levels is noticed by ELISA in the serum of 21 and 41-day-old birds administered with the formulation. Furthermore, humoral immunological response is also improved.

Serum Amyloid A (SAA) is an acute phase protein (APP) that is commonly used as biomarkers of inflammation in chicken serving as a diagnostic tool. Moreover, it is also used to evaluate the response to anti-biotics in poultry. Analysis of SAA in poultry was done using SAA ELISA kit, for which the blood samples were collected from the jugular vein from 10 chickens infected from Newcastle disease and 10 different chickens that were administered (in 4 doses from day 5 to 20 at 5 days interval) with immunostimulant formulation of T2 (400 μl) on day 20th and 30th day. The chickens from which the blood samples were taken were tagged and same chicken were used for sampling on day 30.

Table 9, below, shows the serum amyloid A concentration in control and treated poultry birds.

TABLE 9

| Sample | Control | | Treated (T2-400 μl) | |
|---|---|---|---|---|
| No. | Day 20 | Day 30 | Day 20 | Day 30 |
| 1 | 28.94 ± 0.20 | 34.63 ± 0.10 | 27.21 ± 0.10 | 12.11 ± 0.53 |
| 2 | 41.00 ± 1.08 | 39.30 ± 0.65 | 31.14 ± 0.82 | 20.05 ± 0.47 |
| 3 | 28.94 ± 0.26 | 37.41 ± 0.32 | 22.43 ± 0.11 | 14.71 ± 0.31 |
| 4 | 35.14 ± 1.98 | 38.91 ± 0.82 | 28.15 ± 0.45 | 13.46 ± 0.52 |
| 5 | 23.01 ± 0.83 | 41.11 ± 0.10 | 30.21 ± 0.89 | 19.77 ± 0.18 |
| 6 | 35.04 ± 0.12 | 33.14 ± 0.19 | 20.42 ± 1.20 | 8.05 ± 0.17 |
| 7 | 42.00 ± 1.02 | 39.11 ± 0.21 | 18.77 ± 0.92 | 10.62 ± 0.28 |
| 8 | 29.00 ± 0.12 | 38.92 ± 0.82 | 26.19 ± 0.33 | 14.45 ± 1.00 |
| 9 | 36.00 ± 0.32 | 43.05 ± 0.21 | 30.02 ± 0.10 | 21.21 ± 0.15 |
| 10 | 31.00 ± 0.19 | 32.12 ± 0.55 | 31.12 ± 0.41 | 10.12 ± 0.22 |

*All values are mean of three replications

SAA is a rapidly changing acute-phase protein and it increases with severity of infection. Its levels may increase to a greater extent. From the above table, it is clearly evident that the levels of SAA have increased in control chickens, whereas in chickens administered with the immunostimulant formulation have shown significant reduction in the levels of SAA. This result is also in line with the results of antibody test, where the antibody levels increased in chickens administered with the formulation of the present invention.

The present formulation can be an ideal candidate for the integrated control of wide spectrum of pathogens in poultry birds (broilers and layers) by overcoming the issue of antibiotic resistance.

As all the ingredients are bio-safe molecules and the formulation does not leave any chemical residues in the poultry products, such as egg and meat, thereby making poultry products safe for human consumption.

In a non-limiting illustrative embodiment, the method of preparation of the stable and bioavailable immuno-stimulant herbal formulation of the present invention comprises steps:

(a) preparing an active ingredients blend encapsulated in polysorbate, wherein the active ingredients comprise curcumin, withanolides, eugenol and thymol, the preparation comprising the steps of:
   i. dissolving curcumin in weight percentage range of 0.2 to 0.5% in polysorbates with sonication;
   ii. dissolving withanolides in weight percentage range of 0.2 to 0.3% in water;
   iii. dissolving thymol and eugenol in ethanol, wherein the weight percentage of thymol and eugenol is in range of 0.3 to 0.5% and 0.2 to 0.3% respectively; and
   iv. adding solution (ii) to (i) followed by solution (iii) and thoroughly homogenizing using high sheer homogenizer;

(b) preparing the polymer matrix using chitosan (0.1%) and whey protein (0.05%) at a ratio of 2:1;

(c) separately preparing the amino acid mixture of glycine, lysine, glutamine and tryptophan in the ratio of 5:4:2:1 in water;

(d) adding the active ingredient blend encapsulated in polysorbate obtained in step (a) to the polymer matrix obtained in step (b);

(e) adding amino acid mixture obtained from step (c) to the solution of step (d) and homogenizing at 600-800 rpm;

(f) subjecting the solution of step (e) to sonication for 10-20 minutes to ensure homogenized particle distribution; and (g) optionally adding anti-microbial agents in the solution obtained in step (f) prior to bottling.

The formulation is stable and may be measured by tests as per USP guidelines.

Bioavailability of the formulation (pharmacodynamics and pharmacokinetics) may be studied using an avian model. The formulation, administered orally in cattle, may be efficient with high bioavailability.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. An immuno-stimulant herbal formulation comprising plant bioactive molecules and an essential amino acid encapsulated in a polymer composite, wherein the plant bioactive molecules comprise curcumin, withanolides, thymol and eugenol or the plant bioactive molecules comprise curcumin, safed musli extract, thymol and oregano oil wherein the curcumin is in the range of 2000 to 5000 ppm, the withanolides is in the range of 2000 to 3000 ppm, the thymol is in the range of 3000 to 5000 ppm and the eugenol is in the range of 2000 to 3000 ppm.

2. The immuno-stimulant herbal formulation according to claim 1, wherein the amino acid is selected from glycine, lysine, glutamine, tryptophan, or mixture thereof.

3. The immuno-stimulant herbal formulation according to claim 1, wherein the polymer composite is a chitosan and whey protein.

4. The immuno-stimulant herbal formulation according to claim 1, wherein the amino acid is in the range of 1000 to 5000 ppm.

5. The immuno-stimulant herbal formulation according to claim 2, wherein the amino acid comprises a mixture of glycine, lysine, glutamine and tryptophan in a ratio of 5:4:2:1.

6. The immuno-stimulant herbal formulation according to claim 1, wherein the particle size of the plant bioactive molecules alone is about 10-50 nm.

7. The immuno-stimulant herbal formulation according to claim 1, wherein the particle size of the encapsulated herbal formulation is in the range of about 10-100 nm.

8. A method of treating poultry birds and cattle to enhance an immunity therein, the method comprising administering an effective amount of the immune-stimulant herbal formulation according to claim 1, to one or more of the poultry birds and the cattle.

9. The method of treating poultry birds and cattle according to claim 8, wherein:

the poultry bird is selected from chicken, turkey, duck, goose, guinea fowl, quail and pigeon; and the cattle is selected from cow, ox, bull, calf, sheep and goat.

* * * * *